(12) United States Patent
Kleeven

(10) Patent No.: US 11,071,462 B2
(45) Date of Patent: Jul. 27, 2021

(54) DEVICE AND METHOD FOR THERMAL IMAGING OF A LIVING MAMMAL BODY SECTION

(71) Applicant: DELSENI HOLDING B. V., Weert (NL)

(72) Inventor: Antonius Maria Kleeven, Horst (NL)

(73) Assignee: DELSENI HOLDING B.V., Weert (NL)

( * ) Notice: Subject to any disclaimer, the term of this patent is extended or adjusted under 35 U.S.C. 154(b) by 82 days.

(21) Appl. No.: 16/347,044

(22) PCT Filed: Sep. 19, 2017

(86) PCT No.: PCT/NL2017/050616
§ 371 (c)(1),
(2) Date: May 2, 2019

(87) PCT Pub. No.: WO2018/056806
PCT Pub. Date: Mar. 29, 2018

(65) Prior Publication Data
US 2020/0187785 A1 Jun. 18, 2020

(30) Foreign Application Priority Data

Sep. 22, 2016 (NL) ...................... 2017511

(51) Int. Cl.
*A61B 5/01* (2006.01)
*A61B 5/00* (2006.01)

(52) U.S. Cl.
CPC ............... *A61B 5/01* (2013.01); *A61B 5/004* (2013.01); *A61B 5/4866* (2013.01); *A61B 5/683* (2013.01);
(Continued)

(58) Field of Classification Search
CPC ......... A61B 5/01; A61B 5/004; A61B 5/0086; A61B 5/4866; A61B 5/683; A61B 5/6843;
(Continued)

(56) References Cited

U.S. PATENT DOCUMENTS 4,624,264 A 11/1986 Sagi
6,419,636 B1 * 7/2002 Young ................... A61B 5/015
600/372
(Continued)

FOREIGN PATENT DOCUMENTS

DE 2822636 A1 11/1979
EP 0059328 A1 9/1982
(Continued)

OTHER PUBLICATIONS

International Search Report for International Application No. PCT/NL2017/050616 filed on Sep. 19, 2017 on behalf of MITO Medical Products B.V. Jun. 7, 2018 4 pages.
(Continued)

*Primary Examiner* — Devin B Henson
(74) *Attorney, Agent, or Firm* — Browdy and Neimark, PLLC

(57) ABSTRACT

A device of and a method for obtaining thermal images of a living mammal body section. The device comprises a thermal energy storage surface structure for contacting the body section. In a calibration mode of operation, the thermal energy storage surface structure is brought at a reference temperature by transferring thermal energy to the thermal energy storage surface structure from a thermal energy transfer module that is controlled by a control circuit for restraining thermal energy transfer by the thermal energy transfer module in the presence of the body section at the thermal energy storage surface structure. In a registration
(Continued)

mode of operation, by a thermal sensor, thermal images reflecting thermal energy storage over at least a portion of the thermal energy storage surface structure are obtained, with the body section contacting the thermal energy storage surface structure. From a series of time consecutive thermal images obtained, a region of interest is determined, based on storage of thermal energy by the thermal energy storage surface structure.

22 Claims, 4 Drawing Sheets

(52) U.S. Cl.
CPC .... *A61B 5/6843* (2013.01); *A61B 2562/0271* (2013.01)

(58) Field of Classification Search
CPC .................. A61B 5/015; A61B 5/4312; A61B 2562/0271; G06T 2207/10048; G01K 13/002
See application file for complete search history.

(56) References Cited

U.S. PATENT DOCUMENTS

| | | | |
|---|---|---|---|
| 6,950,693 B1 | 9/2005 | Wehberg | |
| 8,602,642 B2 * | 12/2013 | Klewer | G01K 7/42 374/45 |
| 2007/0213617 A1 | 9/2007 | Berman et al. | |
| 2013/0331683 A1 | 12/2013 | Wehberg | |
| 2014/0276091 A1 * | 9/2014 | Angott | A61B 5/015 600/474 |
| 2017/0027450 A1 * | 2/2017 | Toledano | A61B 5/0048 |
| 2019/0183350 A1 * | 6/2019 | Bonmarin | A61B 5/443 |

FOREIGN PATENT DOCUMENTS

| | | |
|---|---|---|
| WO | 00/64332 A1 | 11/2000 |
| WO | 2009/083974 A1 | 7/2009 |
| WO | 2014/113681 A1 | 7/2014 |
| WO | 2015/159284 A1 | 10/2015 |

OTHER PUBLICATIONS

Stasiek J. et al., "Liquid crystal thermography and true-color digital image processing", Optics and Laser Technology vol. 38 pp. 243-256 (Aug. 10, 2005).

Written Opinion for International Application No. PCT/NL2017/050616 filed on Sep. 19, 2017 on behalf of MITO Medical Products B.V. Jun. 7, 2018 6 pages.

\* cited by examiner

DEVICE AND METHOD FOR THERMAL IMAGING OF A LIVING MAMMAL BODY SECTION

CROSS-REFERENCE TO RELATED APPLICATIONS

The present application is the U.S. National Stage of International Patent Application No. PCT/NL2017/050616 filed on Sep. 19, 2017 which, in turn, claims priority to Netherlands Patent Application No. 2017511 filed on Sep. 22, 2016.

TECHNICAL FIELD

The present invention relates generally to the field of thermal imaging and, more particularly, to a device and method for thermal imaging of a body section of a living mammal, in particular a human being, for determining a region of interest of such body section based on thermal parameters obtained from thermal imaging data.

BACKGROUND

Living biological bodies are subject to metabolic activity. Metabolic activity refers to the set of chemical reactions that maintain life in any organism. Metabolic activity involves the transformation of energy and matter in the body, two elements that always are present for life to be sustained.

Metabolism is associated with heat production. It has been observed that the metabolism of healthy cells of a living body differs from the metabolism of tumour cells—either benign or malignant tumour cells such as cancer cells—in that tumour cells comprise a higher amount of thermal energy. This thermal energy is transferred from the body to its environment in the form of heat.

Nutrients and oxygen required for tumour cell growth results in the formation of new blood vessels in the dermis at the base of a tumour, this because an adequate blood vascular system is necessary for effective tumour cell proliferation. A phenomenon also known as tumour vascularity or hyper vascularity, i.e. an increased number or concentration of blood vessels at a tumour. Many tumours are malignant because of hyper vascularity enabling rapid growth. Grades of tumour vascularity may be qualified as sparse, moderate and prominent. Tumour vascularity as well causes a temperature increase in a living body section compared to its healthy environment.

It will be appreciated that the presence of an inflammation in a living body also gives rise to a locally higher body temperature.

Over the years, several devices have been developed and proposed for detecting anomalies in cells of living bodies, such as tumours, based on the difference in thermal energy emanating from tumour cells compared to healthy cells or tissue.

International patent application WO 2015/159284 A1 discloses a device and method for cancer detection, using active thermal imaging by heating or cooling a body or tissue to be examined, and subsequently collecting thermal data of at least a portion of the thus heated or cooled body.

International patent application WO 2009/083974 A1 discloses a method and apparatus for analysing thermal images obtained by a thermospatial imaging system in which a person is positioned at a platform relative to and remote from a thermographic imaging device.

International patent application WO 00/64332, equivalent to U.S. Pat. No. 6,950,693, discloses a device for thermal imaging of a body section using a thermo-optical foil positioned on a frame. Such a thermo-optical foil assumes different colours as a function of the temperature of the foil. The placement of the thermo-optical foil against a body section results in a heat pattern, represented by different colours, corresponding to the different thermal states of the body section. Also called thermography. These colours are imaged by a digital visible light camera.

In a first, or calibration mode, the thermo-optical foil and the body section have to be cooled to a standardized and constant temperature, lower than the body temperature, thereby reducing the effect of surface or skin heat of the body section on the foil coloration, allowing for standardized and reproducible recording conditions. In a subsequent or registration mode of operation, at the end of a presettable amount of time after the start of the calibration mode, the color pattern of the foil is photographed by the camera and is indicative of temperature differences over the surface of the foil, i.e. over the body section thus imaged.

US patent application 2013/0331683 and German patent application 28 22 636 disclose the use of a thermo-optical foil comprised of a film of Encapsulated Liquid Crystals, ELC.

US patent application 2007/0213617 discloses both a thermospatial imaging system, wherein images of two optical wavelengths, i.e. a first non-penetrating and a second penetrating Infra Red, IR, radiation of the tissue under examination are acquired and correlated for detecting an abnormality, and a typical thermographic tissue examination system, comprising a window or plate having a significant heat capacity for controlling the tissue temperature by cooling or heating up of a tissue portion to be examined.

It has been observed that prior art detection methods and systems based on thermospatial imaging and thermography are less adequate for distinguishing and detecting irregularities in an examined body section. Thermo-optical foils are commercially available in several detection ranges, having a starting registration temperature such as from 28° C., 30° C. and 32° C., for example. Below the starting temperature, the foil is completely black. For detection purposes, based on physical properties of a body to be investigated, such as body weight, age, gender, etc., a particular thermo-optical foil has to be selected. A wrong choice of foil may either result in an excessive coloration or in a too less coloration, both of which do not allow to monitor and detect specific areas of interest.

Like the selection of a suitable foil, assessing the coloration of a thermo-optical foil requires skilled and trained personnel and is for the larger part based on manual interpretation, i.e. by the trained eye. The relative high starting temperature of thermographic detection, among others, makes thermographic registration methods too less specific for detecting anomalies in cells of living bodies, such as tumours, based on the difference in thermal energy emanating from tumour cells compared to healthy cells or tissue. These methods are also too insensitive for detecting tumours deep beneath the surface or skin of the body section and for detecting grades of vascularity, for example.

Vascularity may be effectively detected by Magnetic Resonance Imaging, MRI, using an intravascular contrast agent. This examining method is, however, invasive, relatively time consuming and expensive, and as such not suitable for a relatively quick and easy to use screening for tumour cells, for example.

SUMMARY OF THE INVENTION

It is an object of the invention to provide an improved and easy to use device and method for screening of a living mammal body section, for determining a region of interest, in particular regions or spots of the living body section that may qualify as tumorous or potential tumorous.

Accordingly, in a first aspect of the invention, there is provided a device for obtaining thermal images of a living mammal body section, the device comprising:

a thermal energy storage surface structure for contacting the body section, a thermal sensor for obtaining thermal images reflecting thermal energy storage over at least a portion of the thermal energy storage surface structure in a registration mode of operation of the device, a thermal energy transfer module for transferring thermal energy to the thermal energy storage surface structure for bringing same at a reference temperature in a calibration mode of operation of the device, and a control circuit arranged for monitoring presence of a body section at the thermal energy storage surface structure and for controlling thermal energy transfer by the thermal energy transfer module in the calibration mode in the presence of a body section at the thermal energy storage surface structure for restraining thermal energy transfer by the thermal energy transfer module to the body section.

In the device according to the invention, in the registration mode of operation thereof, for imaging purposes, thermal energy of the body section is transferred to and stored or retained by the thermal energy storage surface structure when in thermal contact with the body section. Images of this energy transfer, i.e. the local change in temperature over at least a portion of the thermal energy storage surface structure, are directly sensed from the thermal energy storage surface structure by a thermal sensor operating on the thermal energy storage surface structure, for capturing images based on the thermal energy stored or retained by the thermal energy storage or thermal energy retaining surface structure.

This provides for an improved sensitivity and specificity, i.e. distinctiveness of the device according to the invention, compared to thermospatial imaging and indirect imaging by the coloration of a thermo-optical foil, for example. In the latter case, the sensitivity of the device is substantially determined by the properties of the thermo-optical foil for transforming thermal energy in a coloration of the foil, which transformation properties have been proven to be insufficient for the purpose of the invention.

In an embodiment of the invention, the thermal energy storage surface structure comprises a thermal energy storage plate or foil, having a flat or curved surface shape, in particular an opaque thermal energy storage plate or foil. For the purpose of the invention, a plate or foil of polyethylene terephthalate, PET, having a thickness in the range of 0.1-1 mm, preferably in a range between 0.2 and 0.7 mm satisfies and shows a sufficient fast response in absorbing and storing thermal energy while investigating a body section.

PET is an excellent water and moisture barrier material, resistant against rubbing alcohol, which is important for medical cleaning and disinfecting purposes, mechanically strong, has a sufficiently high thermal conductivity for absorbing and storing thermal energy and is highly inert, i.e. shows none or a negligible interaction with the skin of a body section under investigation. As an alternative BoPET, biaxially-oriented polyethylene terephthalate, may be used as the thermal energy storage surface structure. PET and BoPET may be coated on a single or both sides with a graphite coating and may be metallized by evaporating a thin film of metal onto its surface, such as aluminium, for example, thereby enhancing the thermal energy absorption and storage properties of the thermal energy storage surface structure.

Prior to the recording of thermal images from the thermal energy storage surface structure, for obtaining reproducible recording conditions in the registration mode of operation, by operation of the thermal energy transfer module, the thermal energy storage surface structure is brought to a reference or starting temperature in a calibration mode of operation of the device according to the invention.

For detecting grades of vascularity, different from the prior art thermography based devices, it has been observed that the body section, i.e. the surface area or skin area thereof, should not be brought, i.e. cooled down or heated up, to this reference or starting temperature of the thermal energy storage surface structure prior to the imaging. Cooling of the body section reduces the blood supply to an anomaly such as a tumour, in that the blood supply capillaries are narrowed, which may obscure a reliable detection of the real expansion of an anomaly, for example. On the other hand, heating up of the body section may raise or stimulate the blood flow in the body section as a whole, thereby reducing the distinctive temperature difference of an anomaly compared to its environment, for example.

To prevent this from occurring, in the calibration mode of operation of the device according to the invention, energy transfer of the thermal energy transfer module to a body section present at the thermal energy storage structure is to be restrained.

To this end, the device according to the invention comprises a control circuit that is arranged for monitoring presence of a body section at the thermal energy storage surface structure. In the presence of a body section at the thermal energy storage surface structure thermal energy transfer by the thermal energy transfer module in the calibration mode is controlled by the control circuit for restraining thermal energy transfer by the thermal energy transfer module to the body section. In this manner, heating up or cooling down of the body section is effectively prevented.

In an embodiment of the device according to the invention, transfer of thermal energy from the thermal energy transfer module to the thermal energy storage surface structure is restrained in that the thermal energy transfer module has a limited thermal energy generation capacity matched to the thermal capacity, i.e. the thermal absorption capacity of the thermal energy storage surface structure, such to bring the thermal energy storage surface structure at the reference temperature in the absence of a body section.

That is, the thermal energy generation capacity of the thermal energy transfer module is not sufficient for bringing the thermal energy storage surface structure at the reference temperature when at the same time a body section is in thermal contact with the thermal energy storage surface structure. Thereby automatically and effectively limiting the transfer of thermal energy with a body section.

In a further embodiment of the device according to the invention, in addition to or as an alternative for the restricted or limited thermal capacity of the thermal energy transfer module, the control circuit may operate at least one of a group including:

a proximity detector for detecting proximity of a body section at the thermal energy storage surface structure, a contact detector for detecting physical contact of a body section with the thermal energy storage surface structure, and a thermal energy transfer detector for detecting deviation of thermal energy transfer by the thermal energy transfer module.

The control circuit, in the calibration mode of operation of the device, when detecting a body section at or close to the thermal energy storage surface structure by one or plural of the proximity detector, the contact detector and the thermal energy transfer detector, may operate on the thermal energy transfer module for affecting the production of thermal energy by limiting or interrupting, for example, the supply of electric energy to the thermal energy transfer module in case of an electrically operated thermal energy transfer module, for example. In addition or as an alternative, the control circuit may operate on the manner in which the thermal energy is transferred from the thermal energy transfer module to the thermal energy storage surface structure, for example by changing thermal resistance in the thermal energy transfer path there between.

In an embodiment of the invention, the control circuit comprises a data processing device operatively connected to the thermal energy transfer module, the processing device being arranged for:

operating the thermal energy transfer module for transferring thermal energy by the thermal energy transfer module to the thermal energy storage surface structure for bringing same at the reference temperature in the calibration mode in the absence of a body section at the thermal energy storage surface structure monitored by the control circuit, operating the thermal energy transfer module for restraining thermal energy transfer by the thermal energy transfer module in the calibration mode in the presence of a body section at the thermal energy storage surface structure monitored by the control circuit, and operating the thermal sensor in the registration mode when the thermal energy storage surface structure is at the reference temperature.

To assist in the correct usage and operation of the device according to the invention, a signalling module is provided, operatively connected to the processing device, for signalling operation in the calibration mode and operation in the registration mode, respectively. In particular for operating the thermal sensor in the registration mode while the thermal energy storage surface structure is absorbing and storing thermal energy from a body section monitored by the control circuit, and for indicating completion of obtaining of the thermal images.

The thermal images are obtained, in an embodiment of the invention, by a multipoint thermal sensor, in particular a digital pixel type thermal imaging camera remotely arranged from the thermal energy storage surface structure, for obtaining time consecutive thermal images over at least a portion of the thermal energy storage surface structure. In particular a camera having a spatial resolution being a fraction of a region of interest to be determined, such as a commercially available high-definition digital Infra-Red, IR, camera.

The thermal sensor, in particular a digital thermal sensor, in an embodiment of the invention, is operatively connected to the data processing device or is operatively connectable to a further internal or external data processing device for digitally processing obtained thermal images and for determining a region of interest by calculating, from a series of time consecutive thermal images obtained, a heat absorption or heat storage rate over at least part of the portion of the thermal energy storage surface structure. The heat absorption rate may be calculated as a temperature gradient over time, detecting a trend in the temperature profile caused by heat absorption and storage at such part of the thermal energy storage surface structure.

The region of interest may be determined, for example, based on whether the heat absorption rate complies to a set profile of heat absorption rate values. The region of interest may additionally or alternatively be determined, for example, by calculating from a series of time consecutive thermal images temperature differences over at least part of the portion of the thermal energy storage surface structure of which thermal images have been obtained, and whether these temperature differences comply to a set profile of temperature differences.

For determining a region or regions of interest, in particular for screening a body section for tumorous or pre-tumorous anomalies, in a further embodiment of the invention, the data processing device is arranged for calculating a shape and size of an area of the thermal energy storage surface structure at which the heat absorption rate and/or temperature differences complies to a set profile.

The device according to the invention allows for assessment of the registration results in an automated manner, producing repeatable and reliable results, not necessarily requiring trained personnel for making an assessment of the registration data. The data obtained may be subjected to several data filtering techniques and data analysing techniques, inclusive correlation techniques based on externally available data, such as data available in medical files or knowledge bases, like medical libraries or the like.

When using a digital pixel type thermal imaging camera as thermal sensor in the device according to the invention, the heat absorption rate and/or temperature differences may be calculated on a pixel basis or from a group of adjacent pixels. The heat absorption rate profiles, heat differences patterns, shapes and sizes of such patterns obtained and further information in support of determining a region of interest, in an embodiment of the invention, are processed by the data processing device using relevant information stored in a digital knowledge base, either a remote or device local knowledge base.

The device may comprise a display module, operatively connected to the data processing device and arranged for displaying at the display module a determined region of interest in a reference frame representing the body section, for example.

In an embodiment of the device according to the invention, the thermal energy transfer module comprises a movably arranged heat conducting plate, having a surface shape adapted for thermally contacting the thermal energy storage surface structure, and a thermogenerator for bringing the heat conducting plate at a temperature for exchanging heat with the thermal energy storage surface structure when in thermal contact therewith, for bringing the thermal energy storage surface structure at the reference temperature.

In particular the thermal energy transfer module may comprises a heatsink arranged opposite the heat conducting plate and a plurality of thermoelectric components distributed across the heatsink, such as so-called Peltier elements, distributed across an attached to the heatsink. In operation, the thermal energy transfer module is arranged for bringing the thermal energy storage surface structure at a reference temperature in a range of 20-30° C., preferably in a range of 24-26° C. The actual reference temperature may be measured using the thermal sensor.

In a second aspect the invention provides a method of determining a region of interest of a living mammal body section based on thermal imaging, the method comprising a calibration mode of operation for bringing a thermal energy storage surface structure at a reference temperature by transferring thermal energy to the energy storage surface structure by a thermal energy transfer module, and a registration mode of operation, following the calibration mode of operation, for obtaining thermal images reflecting thermal energy storage by energy absorption over at least a portion of the thermal energy storage surface structure, the method controlled by a data processing device comprising the steps of:

in the calibration mode of operation:
  detecting presence of a body section at the thermal energy storage surface structure, and
    if present, controlling thermal energy transfer by the thermal energy transfer module for restraining thermal energy transfer to the body section,
    if absent, bringing the thermal energy storage surface structure at the reference temperature,
in the registration mode of operation:
  obtaining time consecutive thermal images of the portion of the thermal energy storage surface structure while storing thermal energy from the body section at the thermal energy storage surface structure, and
  calculating, from a series of time consecutive thermal images obtained, a region of interest based on storage of thermal energy by the thermal energy storage surface structure.

These and other aspects of the invention will be apparent from and elucidated with reference to the embodiment described hereinafter.

DETAILED DESCRIPTION

Figure 1:
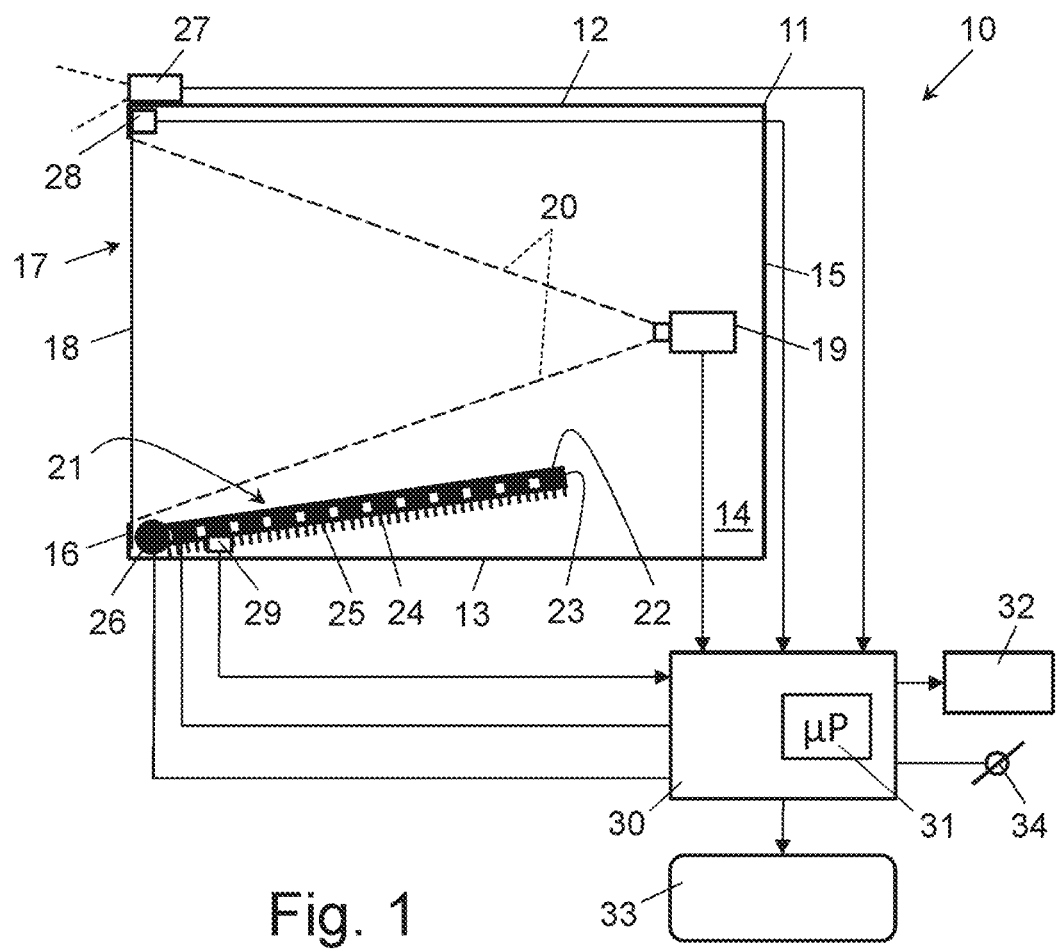
FIG. 1 shows schematically, in a cross-sectional view, an embodiment of an example of a device in accordance with the invention.

FIG. 1 shows a cross-sectional view of an embodiment of a device 10 for obtaining thermal images of a living mammal body section in accordance with the invention. The device 10 has a housing 11, generally comprised of a top part or wall 12, an opposing bottom part or wall 13, two opposing side parts or walls 14, a back part or wall 15 and an open front part or wall 16, when viewed in the operating position of the device 10 as shown FIG. 1. An opening 17 of the front part 16 is covered by a thermal energy storage surface structure 18, such as a thermal energy storage plate or foil, having a flat or curved surface shape, in particular an opaque thermal energy storage plate or foil, for contacting the body section to be imaged.

In the housing 11, near the back part 15 thereof, a thermal sensor 19 is arranged having field of view 20 direct towards the thermal energy storage surface structure 18, for obtaining thermal images reflecting the storage of thermal energy from at least a portion of the thermal energy storage surface structure 18 in a registration mode of operation of the device 10.

The housing 11, i.e. the walls 12, 13, 14, 15, 16 thereof are constructed and arranged to avoid as much as possible radiation of thermal energy towards the thermal sensor from external heat sources, for example.

Any commercially available thermal sensor 19 suitable for capturing a series of thermal or temperature images of the thermal energy storage surface structure 18 with a sufficient accuracy, may be considered for use with the invention. In an embodiment of the invention, the thermal sensor 19 is a multipoint thermal sensor for sensing surface spots or points, i.e. pixels, of the thermal energy storage surface structure 18, in particular a digital pixel type thermal imaging camera, arranged for obtaining time consecutive thermal images over at least a portion of the thermal energy storage surface structure 18. In particular a camera having a spatial resolution for imaging a fraction of a Region of Interest, ROI, to be determined, such as a commercially available high-definition digital Infra-Red, IR, camera.

For the purpose of the invention any plate or foil that sufficiently quickly absorbs and stores or retains or accumulates thermal energy is applicable. The term sufficiently quickly is to be construed in the light of obtaining a series of time consecutive thermal images by the thermal sensor 19. That is, that the thermal energy storage surface structure 18 has heat conducting and heat absorbing properties such to accumulate heat from a body section contacting the thermal energy storage surface structure 18 for calculating a thermal energy absorption rate or transfer rate of thermal energy from the body section under investigation using images captured by the thermal sensor in a particular time period, for example.

In a practical embodiment of the invention, images are taken at a relatively high speed with an interval between consecutive registrations of about 10-100 msec. The total registration time of an investigation or screening of a body section in the registration mode of operation comprises between 30-60 seconds.

In an embodiment of the invention, a plate or foil of polyethylene terephthalate, PET, having a thickness in the range of 0.1-1 mm, preferably in a range between 0.2 and 0.7 mm has been proven to combine a relatively small thermal capacity with a sufficient fast response in absorbing and storing or accumulating thermal energy from a body section under investigation. The plate or foil may be coated on a single or both sides with a thin graphite coating. For localizing a region of interest in the body section from images obtained, the thermal energy storage surface structure 18 should be sufficient mechanically sturdy, i.e. should provide sufficient resistance to deformation from the force by which a body section contacts the thermal energy storage surface structure 18. PET or biaxially-oriented polyethylene terephthalate BoPET combines a relatively thin surface thickness, such as 0.2 mm, with a high mechanical deformation resistance or strength.

In the housing 11 a thermal energy transfer module 21 is arranged, for transferring thermal energy to the thermal energy storage surface structure 18 for bringing same at a reference temperature in a calibration mode of operation of the device 10.

In the embodiment shown in FIG. 1, the thermal energy transfer module 21 is comprised of a movably arranged heat conducting plate 22, having a surface shape adapted for completely contacting the thermal energy storage surface structure 18, and a thermogenerator 23 for bringing the heat conducting plate 22 at a temperature for exchanging heat with the thermal energy storage surface structure 18 when in thermal contact therewith. This, for bringing the thermal energy storage surface structure 18 at a reference temperature in a range of 20-30° C., preferably in a range of 24-26° C. when investigating a human body section, for example.

In an embodiment of the invention, the thermal energy transfer module 21 comprises a heatsink 24 arranged opposite the heat conducting plate 22 such that the thermogenerator 23 is comprised between the heat conducting 22 and the heatsink 24 and is constructed of a plurality of thermoelectric components 25, such as so-called Peltier elements, distributed across the heatsink.

A Peltier element or thermoelectric heat pump is a solid-state active device that transfers heat from one side of the device to the other, with consumption of electrical energy, depending on the direction of the electric current flowing through the device. Commercially available Peltier elements can be used either for heating or for cooling of an object and is also called a Peltier heat pump, solid state refrigerator, or ThermoElectric Cooler, TEC.

In the embodiment shown, the thermal energy transfer module 21 is pivotally supported at the bottom wall 13 and near the front wall 16 of the housing 11, over its entire length as seen in the direction perpendicular to the plane of the drawing, i.e. between the sidewalls 14 of the housing 11. For moving the thermal energy transfer module 21 from the position near the bottom wall 13 as shown in FIG. 1 to the position for contacting the thermal energy storage surface structure 18 near the front wall 16 of the housing 11, drive means are arranged with and operate on the pivotal support, as indicated by reference numeral 26. Suitable drive means 26 may include an electric motor such as a servo motor.

The thermal sensor 19, the thermogenerator 23, i.e. the thermoelectric components 25 thereof, and the drive means 26 operatively connect to a control circuit 30, for controlling operation of the device 10. The control circuit 30 may comprise a programmable data processing device 31, such as a microcontroller, microprocessor or microcomputer or the like.

In an embodiment of the invention, the thermal energy transfer module 21 has a limited thermal generation capacity matched to the thermal energy storage surface structure 18, such to bring the thermal energy storage surface structure 18 at the reference temperature in the absence of a body section. This to limit the transfer of thermal energy from the thermal energy transfer module 21 to a body section in contact with thermal energy storage surface structure 18, in the calibration mode of operation of the device, such to prevent inadvertently heating or cooling of the body section before its investigation in the registration mode of operation of the device 10.

In a further embodiment of the invention, the device 10 comprises one or a plurality of a proximity detector 27, for detecting proximity of a body section at or near the thermal energy storage surface structure 18, such as a photo-electric detector, an IR detector, a capacitive detector and the like. A contact detector 28, for detecting physical contact of a body section with the thermal energy storage surface structure 18, such as a strain gauge detector for measuring strain exerted by a body section contacting the thermal energy storage surface structure 18, and/or a thermal energy transfer detector 29, such as a temperature detector, for detecting deviation of thermal energy transfer by the thermal energy transfer module 21, for example from a temperature step or a power consumption step of the thermogenerator 23.

For control and operation purposes, the detectors 27, 28, 29 operatively connect to the control circuit 30. The control circuit 30 is arranged for disconnecting or interrupting operation of the thermogenerator 23 when detecting the presence of a body section in the vicinity of the thermal energy storage surface structure 18 and/or contact of a body section with thermal energy storage surface structure 18 and/or detecting an anomaly in the transfer of thermal energy by the thermal energy transfer detector 29 from the thermal energy transfer module 21, in the calibration mode of operation of the device 10, for example.

The device 10 may comprise, in an embodiment, a signalling module 32, operatively connected to the control circuit 30, i.e. the processing device 31 thereof, for externally signalling operation of the device 10 in the calibration mode and operation in the registration mode, respectively. In particular for signalling operation of the thermal sensor 19 in the registration mode of operation of the device 10, while the thermal energy storage surface structure 18 is storing thermal energy from a body section monitored by the device 10, and for indicating completion of obtaining thermal images by the thermal sensor 19. The signalling module 32 may comprise any of an acoustic, optical or other type of signalling module.

It is noted that the control circuit 30 may operate in a so-called stand alone mode wherein the data registered by the thermal sensor 19 are processed by the control circuit 30, i.e. the data processing device 31 thereof, in accordance with a processing algorithm or algorithms for calculating a region of interest at a body section under investigation from a series of time consecutive thermal images obtained by the thermal sensor 19 from the storage of thermal energy by the thermal energy storage surface 18 in the registration mode of operation of the device 10. To this end, the control circuit may operate a display device 33, for presenting a region of interest thus calculated, for example, in a graphical manner and/or supported by a table of measured and/or calculated results. The control circuit 30 and data processing device 31, the signalling module 32 and the display device 33 may be incorporated in the housing 11 of the device 10 or may be provided as a separate module remote from but operatively connected to the device 10.

Instead of or in addition to operation of the control circuit 30 in a stand alone mode, data measured by the thermal sensor 19 and/or calculated by the processing device 31 may be processed in a processing device external from the control circuit 30, for example an external computer to which the control circuit 30 connects via a data communication network and a data interface 34, for example. The data interface 34 may also serve as input/output for controlling operation of the device 10 and/or programming the data processor device 31, for example.

Operation of the device 10 for investigating a body section 35 is schematically illustrated by means of FIGS. 2-5 which show part of the device 10 of FIG. 1 for illustrating the several operational modes of the device in accordance with an embodiment of the invention. For clarity reasons, the detectors 27, 28 29, the control circuit 30, the signalling module 32 and the display device 33 are not shown.

For the purpose of illustrating the operation of the invention, the body section 35 is shown comprising an irregularity 36 such as a tumour beneath the surface or skin 37 of the body section 35, producing thermal energy that is emitted as heat, schematically indicated by arrows 38. The heat 38 is transferred from the body section 35 to the environment. It will be appreciated that in general the irregularity 36 is not known beforehand and it has to be detected by investigating the body section 35 in accordance with the invention and/or whether this irregularity qualifies as a region of interest.

Figure 2:
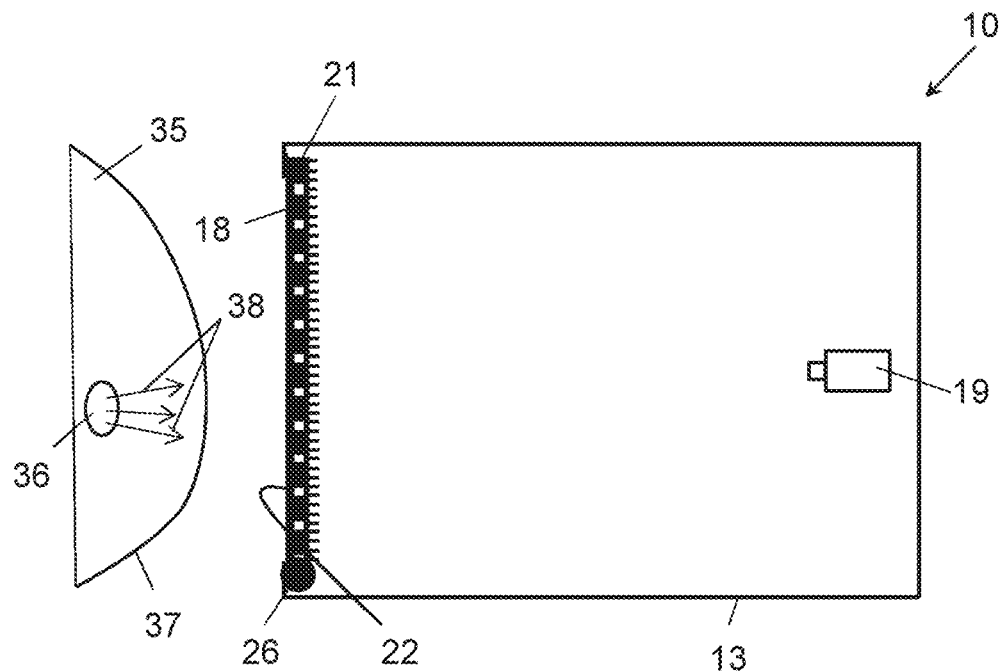
FIGS. 2-5 shows the device of FIG. 1 in several operational modes in accordance with an embodiment of the invention.

In a first step or calibration mode of operation of the device 10, as shown in FIG. 2, the thermal energy transfer module 21 is moved by the drive means 26 in a position such that the heat conducting plate 22 is in contact with the thermal energy storage surface structure 18. The thermal energy transfer module 21 is operated by the control circuit 30 for transferring thermal energy to the thermal energy storage surface structure 18 to bring same at a reference temperature in the absence of the body section 35. That is, the body section 35 is at such a distance from the thermal energy storage surface structure 18 that the temperature of the body section 35 is not influenced or altered by the thermal energy transfer module 21. Absence of the body section is monitored by any or more of the sensors 27, 28, 29, as explained above. Thermal energy transfer is restrained when sensing presence of a body section 35 at said thermal energy storage surface structure 18, monitored by the control circuit 30.

The purpose of the calibration mode of operation is to reset the thermal energy storage surface structure 18 to a reference or starting temperature. The thermal energy transfer module 21 is kept in the position shown in FIG. 2 for a sufficient long time to ensure that the entire thermal energy storage surface structure 18 is brought to the reference temperature. In general, the thermal energy transfer module 21 is operated to cool down the thermal energy storage surface structure 18 to a reference temperature in a range between about 20-30° C.

The reference temperature need not to be pre-set, but can be determined by the thermal sensor 19 from plural point measurements spread over the surface of the thermal energy storage surface structure 18. It is important that after the reset the entire surface of the thermal energy storage surface structure 18 is at a same temperature.

Figure 3:
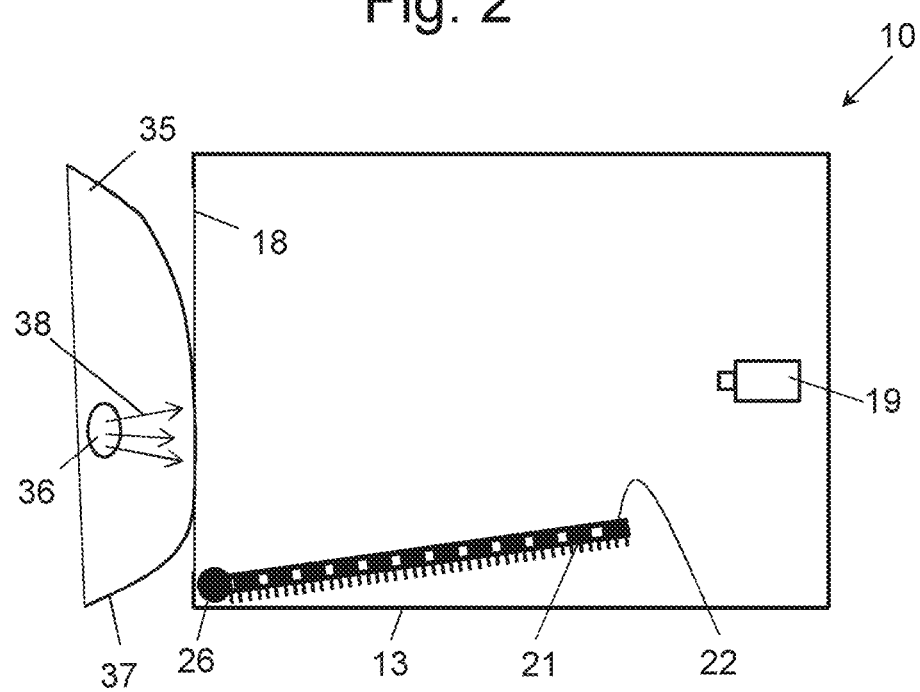
Figure 4:
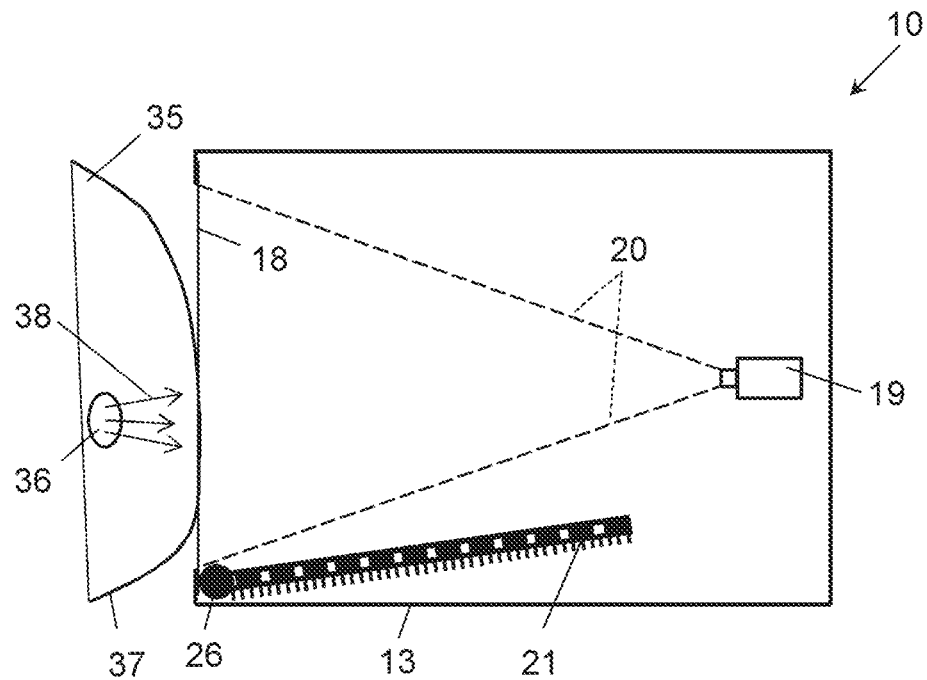

In a second step, as shown in FIG. 3, the thermal energy transfer module 21 is switched off and moved towards a position near the bottom wall 13 of the housing 11. The body section 35 is now brought into contact with thermal energy storage surface structure 18. The start of this step may be signalled by the signalling module 32 indicating when the thermal energy storage surface structure 18 is at the reference temperature and if the thermal energy transfer module 21 is moved away from the thermal energy storage surface structure 18.

In the case that the reference temperature of the thermal energy storage surface structure 18 is below the temperature of the body section, such as with a living human body section having a body temperature of, for example, 35-38° C., thermal energy will be transferred from the body section 35 to the thermal energy storage surface structure 18, resulting in a gradual temperature increase thereof. In the event that the reference temperature, at the start of the registration mode, is above the body temperature, the temperature of the thermal energy storage surface structure 18 will decrease.

In a third step or registration mode of operation, the thermal sensor 19 is operated to register thermal energy originating from the body section 35 that is stored at the thermal energy storage surface structure 18. It will be appreciated that the thermal energy stored at the area of the thermal energy storage surface structure 18 that is in contact with part of the skin 37 where thermal energy 38 of the irregularity 36 is exchanged, will deviate from other parts of the thermal energy storage surface structure 18. Operation of the thermal sensor 19 is schematically indicated by the broken lines 20 representing the field of view of the thermal sensor 19.

During the registration mode of operation, the thermal sensor 19 is operated to obtain a series of time consecutive thermal images from the thermal energy storage surface structure 18 while the body section 35 is in contact with the thermal energy storage surface structure 18. The images, i.e. the data representing the images taken, may be stored and processed at the control circuit 30, i.e. the data processing device 31, and/or at a server or data processing and storage device remote from the location where the investigation of the body section 35 by the device 10 is performed.

The number of images and the frequency by which the images are taken by the thermal sensor and/or the total registration time may be pre-set or dynamically determined or adapted, based on temperature measurements or based on a pre-evaluation of the images that are already taken, for example.

Figure 5:
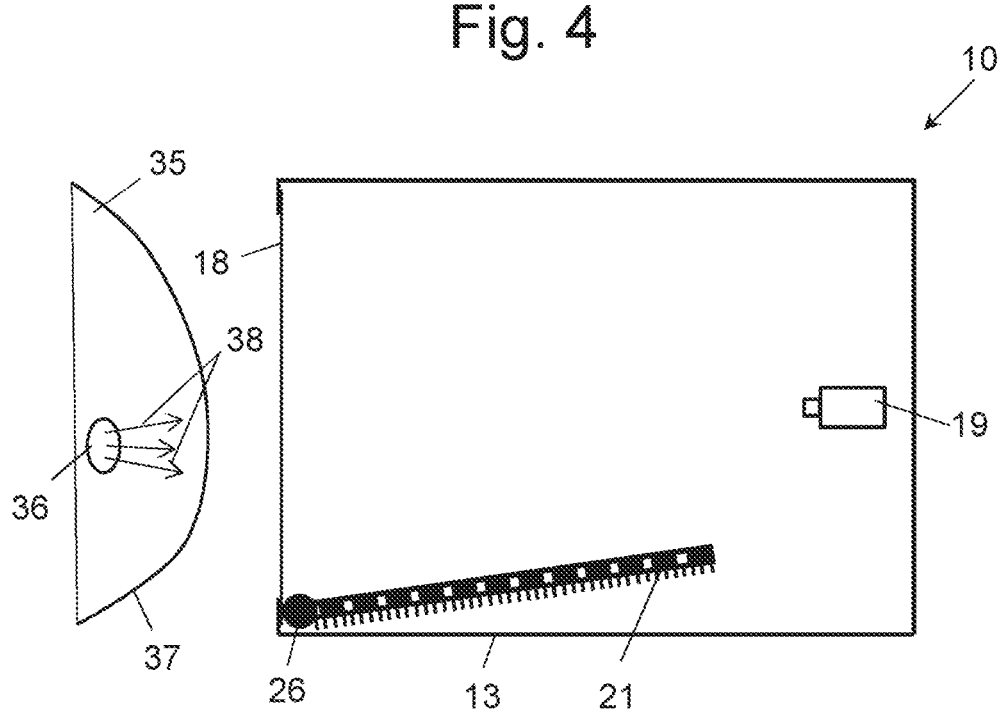

In a fourth step, when the registration mode of operation is completed, which may be signalled by the signalling module 32, for example, registration by the thermal sensor 19 is stopped and the body section may be removed from the thermal energy storage surface structure 18, as illustrated by FIG. 5.

After cleaning of the thermal energy storage surface structure 18 a new investigation may be performed, following the steps outlined above in FIGS. 2-5.

The thermal images obtained by the thermal sensor 19, are processed by the data processing device 31 of the control circuit 30 and/or by a remote data processing device for determining the irregularity 36, in particular for determining whether the irregularity qualifies as a region of interest 36 in the body section 35 in accordance with a pre-set profile or profiles.

To this end, in an embodiment of the invention, from a series of time consecutive thermal images obtained, a heat absorption rate is calculated over at least part of a portion of the thermal energy storage surface structure 18 where storage of thermal energy differs from other parts of the thermal energy storage surface structure 18, for example. As outlined above, in the event of a body section 35 having a body temperature above the reference temperature of the thermal energy storage surface structure 18, it will be appreciated that at and around the area of the thermal energy storage surface structure 18 that is in contact with part of the body section 35 where thermal energy 38 of the irregularity 36 is exchanged, the storage of thermal energy in the thermal energy storage surface structure 18 will deviate from other parts of the thermal energy storage surface structure 18.

These other parts will either show a gradual temperature increase by collecting thermal energy from the body part 35 or a gradual temperature increase or decrease dependent on the ambient temperature at those spots or parts of the thermal energy storage surface structure 18 that are not in contact with the body section 35. A region of interest is now determined based on whether the heat absorption rate complies to a set profile or profiles of heat absorption rate values. The heat absorption rate is calculated as a temperature gradient over time.

Table 1 below shows, by way of example, a registration of temperature differences in a selected area of the thermal energy storage surface structure 18 for eighteen neighbouring spots, numbered 1-18, of the thermal energy storage surface structure 18 as sensed by the thermal sensor 19. In case of a digital pixel type thermal imaging camera used as thermal sensor 19 in the device according to the invention, the heat absorption rate and/or temperature differences may be calculated on a pixel basis or from a group of adjacent pixels forming neighbouring spots. By way of example, the length, width or diameter dimensions of a spot size may range from 0.2-5 mm, for example.

In the column Time of Table 1, the time lapsed between two consecutive registrations or images by the thermal sensor 19 is indicated in milliseconds [msec]. In the example shown, this time amounts 55 msec. In the column Temperature Difference, the temperature difference is indicated that is registered by the thermal sensor 19 over the time period of 55 msec. That is, the temperature difference measured in ° C. between the end of an image and the start of a consecutive next image, at the particular spot indicated by its spot number in the first column of Table 1. A negative temperature difference indicates a drop in the temperature at a particular spot at the thermal energy storage surface structure 18. The calibration temperature of the thermal energy storage surface structure 18, in this example, is 20° C. as indicated in the column Calibration Temperature. The normal or absolute temperature of the body section 35 amounts 35.5° C., as indicated in the column Absolute Temperature.

In the column Heat Absorption Rate, HAR, the heat absorption rate is calculated as a temperature gradient over time, that is the temperature difference divided by the time. The HAR is expressed as [° C./sec]. Note that at spot 15 a large temperature difference of 5° C. over 25 msec is registered. To avoid large numbers, the registration time is automatically limited by the thermal sensor to 25 msec.

TABLE 1

| Spot nr. | Calibration Temperature [° C.] | Temperature Difference [° C.] | Time [msec] | Absolute Temperature [° C.] | HAR [° C./sec] |
| --- | --- | --- | --- | --- | --- |
| 1 | 20.00 | 4.00 | 55 | 35.50 | 72.7 |
| 2 | | 3.50 | 55 | | 63.6 |
| 3 | | 4.21 | 55 | | 76.5 |
| 4 | | 4.22 | 55 | | 76.7 |
| 5 | | 4.22 | 55 | | 76.7 |
| 6 | | 4.45 | 55 | | 80.9 |
| 7 | | 4.44 | 55 | | 80.7 |
| 8 | | 4.56 | 55 | | 82.9 |
| 9 | | 4.56 | 55 | | 82.9 |
| 10 | | 4.65 | 55 | | 84.5 |
| 11 | | 4.80 | 55 | | 87.3 |
| 12 | | 5.43 | 55 | | 98.7 |
| 13 | | 5.65 | 55 | | 102.7 |
| 14 | | 5.80 | 55 | | 105.5 |
| 15 | | 5.00 | 25 | | 200.0 |
| 16 | | 6.00 | 55 | | 109.1 |
| 17 | | 6.10 | 55 | | 110.9 |
| 18 | | 6.20 | 55 | | 112.7 |

Figure 6A:
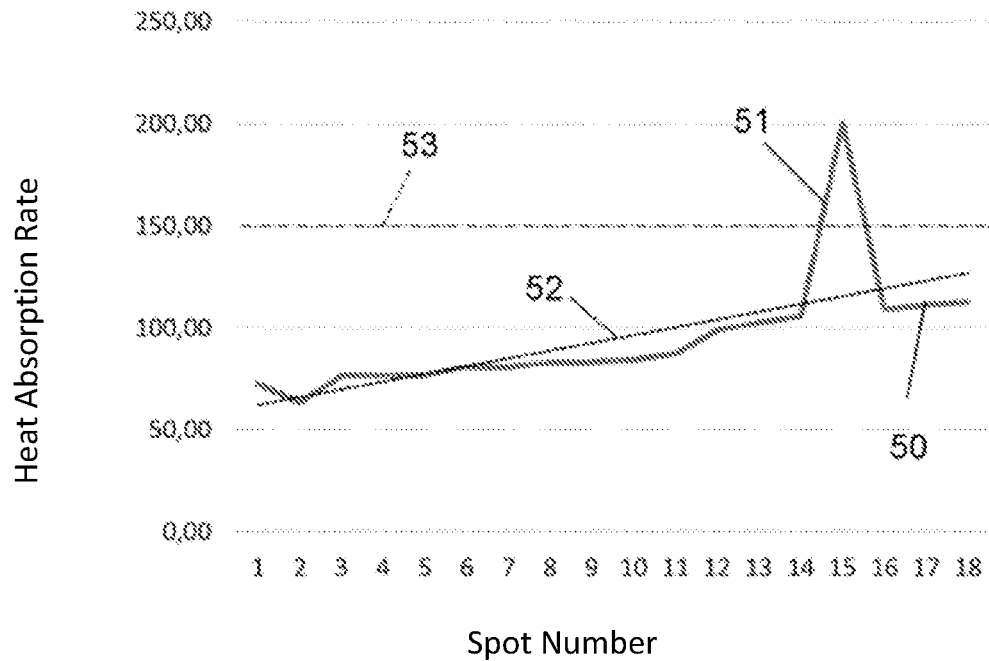
FIGS. 6a and 6b shows an example of a registration curve of thermal energy storage at the thermal energy storage surface in an embodiment of the invention.

The calculated HAR is depicted in a graph 50 shown in FIG. 6a. The Horizontal axis comprises the spot number and the vertical axis shows the HAR expressed in ° C./sec. The sharp peak 51 in the graph 50 around spots 14, 15, 16 clearly differs from the linear regression line or trendline of the HAR over the spots 1-18, depicted by the dotted line 52. By correlating the peak 51 with the position of the body section 35 positioned against the thermal energy storage surface structure 18, it appears that the spots 14, 15, 16 correspond to the irregularity 36 in the body section 35. Because the peak 51 exceeds the HAR threshold or profile 53, shown by a dash-dot line in FIG. 6a, the area of the thermal energy storage surface structure 18 qualifies as a region of interest in accordance with the invention.

TABLE 2

| Spot nr. | Calibration Temperature [° C.] | Temperature Difference [° C.] | Time [msec] | Absolute Temperature [° C.] | HAR [° C./sec] |
| --- | --- | --- | --- | --- | --- |
| 81 | 20.00 | 2.50 | 55 | 35.50 | 45.5 |
| 82 | | 3.50 | 55 | | 63.6 |
| 83 | | 3.89 | 55 | | 70.7 |
| 84 | | 3.91 | 55 | | 71.1 |
| 85 | | 3.99 | 55 | | 72.5 |
| 86 | | 3.74 | 55 | | 68.0 |
| 87 | | 3.80 | 55 | | 69.1 |
| 88 | | 3.12 | 55 | | 56.7 |
| 89 | | 3.56 | 55 | | 64.7 |
| 90 | | 3.88 | 55 | | 70.5 |
| 91 | | 3.90 | 55 | | 70.9 |
| 92 | | 4.01 | 55 | | 72.9 |
| 93 | | 4.22 | 55 | | 76.7 |
| 94 | | 4.31 | 55 | | 78.4 |
| 95 | | 4.34 | 55 | | 78.9 |
| 96 | | 4.54 | 55 | | 82.5 |
| 97 | | 4.56 | 55 | | 82.9 |
| 98 | | 4.71 | 55 | | 85.6 |

Table 2 shows, in addition to Table 1, further measured and calculated HAR results for the body section 35, however relating to a different area thereof, i.e. represented by spot numbers 81-98.

Figure 7:
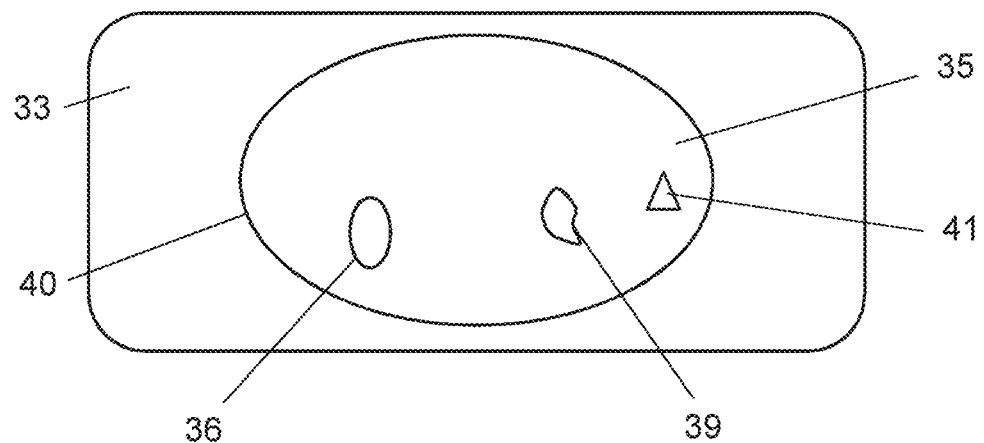
FIG. 7 schematically shows examples of regions of interest in a display of a body section investigated with the device shown in FIGS. 1-5.
Figure 6B:
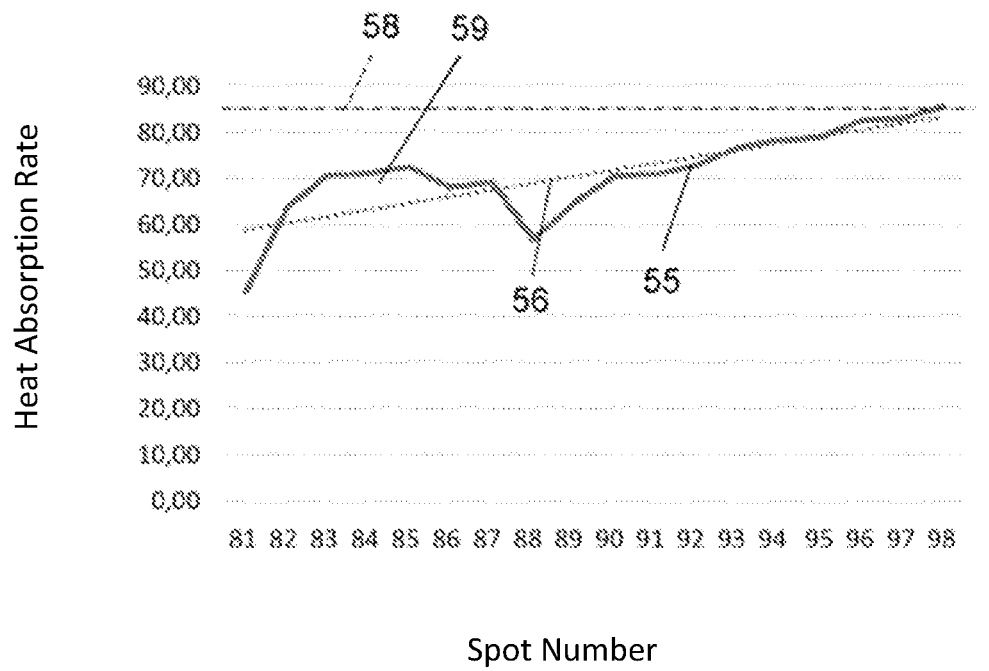

The calculated HAR is depicted in a graph 55 shown in FIG. 6b. The Horizontal axis comprises the spot number and the vertical axis comprises the HAR calculated for a particular spot and expressed in ° C./sec. The increase 57 in the graph 50 around spots 82-87 differs from the linear regression line or trendline 56, depicted by a dotted line. By correlating the area represented by the spots 82-87 and the body section 35 under investigation, it turns out that same corresponds with a further irregularity 39 in the body section 35, as depicted in FIG. 7. FIG. 7 schematically shows the body section 35 in a front view at the display device 33, as viewed from the thermal sensor 19. From the graph 55 in FIG. 6b, it turns out that the increase 57 does not extend beyond the profile 58, indicated by a dash-dot line and therefore does not qualify as a region of interest in accordance with the invention.

In both FIGS. 6a and 6b the profile 53, 58 for determining a region of interest is shown as a straight line. It is, however, also possible to define such a profile as a curved line or otherwise shaped line or area, for example. Further, the profile may be automatically adapted based on physical properties of the body or body section to be investigated, like age, body weight, gender, etc.

In an other embodiment of the invention, a region of interest is determined by calculating, from a series of time consecutive thermal images obtained, temperature differences over at least part of the thermal energy storage surface structure 18 in contact with the body section 35, and wherein a region of interest is determined based on whether the temperature differences comply to a set profile or profiles of temperature differences.

By setting a HAR profile and/or a profile of temperature differences in the form of enclosing an area of the graph, the data processing device may determine a region of interest by calculating from the measurements performed, i.e. the registrations of the thermal sensor 19, a shape and/or a size of an area of the thermal energy storage surface structure at which the heat absorption rate and/or temperature differences complies to a set profile comprising or representing a particular shape and size.

For determining irregularities and regions of interest, besides calculating heat absorption profiles and/or heat difference patterns from the registrations obtained by the thermal sensor 19, information may be used available from a digital knowledge base, either a remote or device local knowledge base comprising information in support of a determined region of interest. Such information may comprise previous calculations of the same or comparable body sections, profiles and medical information, for example.

Correlation of the body section 35, i.e. the geographical position thereof, with the positions or spots at the thermal energy storage surface structure 18 may be performed by obtaining a total temperature image of the body section 35 by the thermal sensor 19, indicating the outer contour 40 of the body section 35, from an external temperature marker 41 positioned at the body section 35, or from a known temperature area at the body section, such as the nipple of male or female breast, for example. An external marker 41 is, for example, a label or sticker of a material having thermal characteristics different from the body section 35, such as piece of metal like aluminium. This to detect the position of the marker 41 in the thermal images of the thermal sensor 19. The shape of the marker 41 preferably deviates from the shape of an anomaly. Circular, triangular, square or other mathematical marker shapes or contours may be used for easy detection purposes.

In the case of a transparent thermal energy storage surface structure 18, such as a surface structure made of PET, a visual image of the body section provided with a marker or markers may be obtained using the thermal sensor and/or a separate visual camera (not shown) that is positional correlated with the thermal sensor 19.

It will be appreciated that the steps of calibrating, registering and analysing of the registered data may be performed completely automatically, without human supervision.

The invention further relates to a computer program, i.e. a computer program product, stored/distributed on a suitable medium, such as an optical storage medium or a solid-state medium supplied together with or as part of other hardware, but may also be distributed in other forms, such as a signal via the Internet or other wired or wireless telecommunication systems.

The invention has been illustrated and described in detail in the drawings and foregoing description in accordance with an embodiment thereof. This illustration and description are to be considered for illustrative and exemplary purposes only. The invention is not limited to or restricted by the disclosed embodiments.

For example, the thermal energy transfer module 21 may be moved to slide away from and in front of the opening or aperture 11, or may pivot along another side wall. Further, within the context of the invention, further mathematical and data analyses techniques may be used for determining a region of interest from the registrations of the thermal sensor than explicitly disclosed above, for example by known regression techniques for calculating trends in the thermal energy storage at the thermal energy storage surface structure 18. For correlating the registrations by the thermal sensor from the thermal energy storage surface structure 18 and the actual position of the body section 35 thereat, three-dimensional images of the body section 35 may be obtained, for example.

Those skilled in the art will appreciate other variations to the disclosed embodiments but comprised by the appended claims from practicing the claimed invention and/or from a study of the description, drawings and claims. In the claims, the word "comprising" does not exclude other elements or steps, and the indefinite article "a" or "an" does not exclude a plurality. A single processor or other digital processing unit may fulfil the functions of several items recited in the claims and features recited in mutually different dependent claims may be combined. Reference signs in the claims are provided for illustrative purposes only.

The invention claimed is:

1. A device for obtaining thermal images representing a living mammal body section, said device comprising:
    a thermal energy storage surface structure that may be brought into proximity to the body section when in use;
    a thermal sensor disposed such that it can obtain thermal images reflecting thermal energy storage over at least a portion of said thermal energy storage surface structure in a registration mode of operation of the device when in use;
    a thermal energy transfer module capable of transferring thermal energy to or from said thermal energy storage surface structure, thereby bringing said thermal energy storage surface structure to a reference temperature in a calibration mode of operation of the device;
    a detector that detects the presence of the body section in proximity to or in contact with said thermal energy storage surface structure; and
    a control circuit programmed to monitor for the presence of the body section in proximity to or in contact with said thermal energy storage surface structure and to control thermal energy transfer by said thermal energy transfer module so as to restrain thermal energy transfer by said thermal energy transfer module to said thermal energy storage surface structure whenever the device is in proximity to or in contact with the body section.

2. The device according to claim 1, wherein said thermal energy transfer module has a limited thermal energy generation capacity matched to a thermal absorption capacity of said thermal energy storage surface structure, for bringing said thermal energy storage surface structure to said reference temperature in the absence of a body section.

3. The device according to claim 1, wherein said control circuit operates said detector and said detector is at least one selected from the group consisting of:
    a proximity detector for detecting proximity of a body section at said thermal energy storage surface structure,
    a contact detector for detecting physical contact of a body section with said thermal energy storage surface structure, and
    a thermal energy transfer detector for detecting deviation of thermal energy transfer by said thermal energy transfer module.

4. The device according to claim 1, further comprising a data processing device operatively connected to said thermal energy transfer module, said data processing device arranged for:
    operating said thermal energy transfer module for transferring thermal energy by said thermal energy transfer module to said thermal energy storage surface structure for bringing same to said reference temperature in said calibration mode in the absence of a body section in proximity to or in contact with said thermal energy storage surface structure monitored by said control circuit,
    operating said thermal energy transfer module for restraining thermal energy transfer by said thermal energy transfer module in said calibration mode in the presence of when a body section at is in proximity to or in contact with said thermal energy storage surface structure monitored by said control circuit, and operating said thermal sensor in said registration mode when said thermal energy storage surface structure is at said reference temperature.

5. The device according to claim 1, further comprising a data processing device operatively connected to said thermal energy transfer module, and a signalling module, operatively connected to said data processing device, for signalling operation in said calibration mode, for signalling operation in said registration mode, and for signalling completion of obtaining said thermal images.

6. The device according to claim 1, wherein said thermal sensor is a multipoint thermal sensor remotely arranged from said thermal energy storage surface structure, for obtaining time consecutive thermal images over at least a portion of said thermal energy storage surface structure.

7. The device according to claim 1, further comprising a data processing device operatively connected to said thermal sensor, said data processing device arranged for processing obtained thermal images and arranged for determining a region of interest by calculating, from a series of time consecutive thermal images obtained, a heat absorption rate over at least part of said portion of said thermal energy storage surface structure.

8. The device according to claim 1, further comprising a data processing device operatively connected to said thermal sensor, said data processing device arranged for processing obtained thermal images, and arranged for determining a region of interest by calculating, from a series of time consecutive thermal images obtained, temperature differences over at least part of said portion of said thermal energy storage surface structure.

9. The device according to claim 1, further comprising a data processing device operatively connected to said thermal sensor, said data processing device arranged for processing obtained thermal images, and arranged for determining a region of interest by calculating, from a series of time consecutive thermal images obtained, a heat absorption rate over at least part of said portion of said thermal energy storage surface structure, wherein said thermal sensor is a digital pixel type thermal imaging camera and said data processing device is arranged for calculating said heat absorption rate on at least one of a pixel basis and a group of adjacent pixels.

10. The device according to claim 1, further comprising a data processing device operatively connected to said thermal sensor, said data processing device arranged for processing obtained thermal images, and arranged for determining a region of interest by calculating, from a series of time consecutive thermal images obtained, a heat absorption rate over at least part of said portion of said thermal energy storage surface structure, wherein said data processing device is arranged for exchanging data of a region of interest with a digital knowledge base, said knowledge base comprising information in support of a region of interest.

11. The device according to claim 1, wherein said thermal energy storage surface structure comprises one of a thermal energy storage plate and a thermal energy storage foil, having a flat or curved surface shape.

12. The device according to claim 1, wherein said thermal energy transfer module comprises a movably arranged heat conducting plate, having a surface shape adapted for thermally contacting said thermal energy storage surface structure, and a thermogenerator for bringing said heat conducting plate at a temperature for exchanging heat with said thermal energy storage surface structure when in thermal contact therewith, for bringing said thermal energy storage surface structure to said reference temperature.

13. The device according to claim 1, wherein said thermal energy transfer module is arranged for bringing said thermal energy storage surface structure to a reference temperature in a range of 20-30° C.

14. The device according to claim 1, wherein said thermal sensor is a digital pixel type thermal imaging camera, remotely arranged from said thermal energy storage surface structure, for obtaining time consecutive thermal images over at least a portion of said thermal energy storage surface structure.

15. The device according to claim 1, further comprising a data processing device operatively connected to said thermal sensor, said data processing device arranged for processing obtained thermal images, and arranged for determining a region of interest by calculating, from a series of time consecutive thermal images obtained, a heat absorption rate over at least part of said portion of said thermal energy storage surface structure based on compliance of said calculated heat absorption rate to a set profile of heat absorption rate values.

16. The device according to claim 1, further comprising a data processing device operatively connected to said thermal sensor, said data processing device arranged for processing obtained thermal images, and arranged for determining a region of interest by calculating, from a series of time consecutive thermal images obtained, a heat absorption rate over at least part of said portion of said thermal energy storage surface structure, wherein said data processing device is arranged for calculating said heat absorption rate as a temperature gradient over time.

17. The device according to claim 1, further comprising a data processing device operatively connected to said thermal sensor, said data processing device arranged for processing obtained thermal images, and arranged for determining a region of interest by calculating, from a series of time consecutive thermal images obtained, temperature differences over at least part of said portion of said thermal energy storage surface structure, wherein said data processing device is arranged for determining said region of interest based on compliance of said temperature differences to a set profile of temperature differences.

18. The device according to claim 1, further comprising a data processing device operatively connected to said thermal sensor, said data processing device arranged for processing obtained thermal images, and arranged for determining a region of interest by calculating, from a series of time consecutive thermal images obtained, temperature differences over at least part of said portion of said thermal energy storage surface structure, wherein said thermal sensor is a digital pixel type thermal imaging camera and said data processing device is arranged for calculating said temperature differences on at least one of a pixel basis and a group of adjacent pixels.

19. The device according to claim 1, further comprising a data processing device operatively connected to said thermal sensor, said data processing device arranged for processing obtained thermal images, and arranged for determining a region of interest by calculating, from a series of time consecutive thermal images obtained, temperature differences over at least part of said portion of said thermal energy storage surface structure, wherein said data processing device is arranged for exchanging data of a region of interest with a digital knowledge base, said knowledge base comprising information in support of a region of interest.

20. The device according to claim 1, wherein said thermal energy storage surface structure comprises one of an opaque thermal energy storage plate and an opaque thermal energy storage foil.

21. The device according to claim 1, wherein said thermal energy transfer module comprises a movably arranged heat conducting plate, having a surface shape adapted for thermally contacting said thermal energy storage surface structure, a heatsink arranged opposite said heat conducting plate, and a thermogenerator for bringing said heat conducting plate to a temperature for exchanging heat with said thermal energy storage surface structure when in thermal contact therewith, for bringing said thermal energy storage surface structure to said reference temperature, said thermogenerator comprising a plurality of thermoelectric components distributed across said heatsink.

22. A method of determining a region of interest of a living mammal body section based on thermal imaging by a device comprising a thermal energy storage surface structure, a thermal sensor for obtaining thermal images reflecting thermal energy storage over at least a portion of said thermal energy storage surface structure, and a thermal energy transfer module, a control circuit programmed to monitor for the presence of a body section in proximity to or in contact with said thermal energy storage surface structure and for controlling thermal energy transfer by said thermal energy transfer module, said method comprising:

a calibration mode of operation comprising causing said thermal energy transfer module to bring said thermal energy storage surface structure to a reference temperature; and a registration mode of operation, following said calibration mode of operation, comprising bringing said thermal energy storage structure into proximity to or in contact with said body section, and using the thermal sensor to obtain thermal images reflecting thermal energy storage over at least a portion of said thermal energy storage surface structure, wherein, in said calibration mode, the thermal energy transfer by said thermal transfer module is restrained when the presence of a body section in proximity to or in contact with said thermal energy storage surface structure is detected.

* * * * *